(12) United States Patent
Boyer

(10) Patent No.: US 6,459,767 B1
(45) Date of Patent: Oct. 1, 2002

(54) PORTABLE X-RAY FLUORESCENCE SPECTROMETER

(75) Inventor: Bradley W. Boyer, Scotts Valley, CA (US)

(73) Assignee: Oxford Instruments, Inc., Scotts Valley, CA (US)

( * ) Notice: Subject to any disclaimer, the term of this patent is extended or adjusted under 35 U.S.C. 154(b) by 0 days.

(21) Appl. No.: 09/770,862

(22) Filed: Jan. 26, 2001

Related U.S. Application Data

(60) Provisional application No. 60/255,223, filed on Dec. 12, 2000.

(51) Int. Cl.⁷ .............................................. H01J 35/06
(52) U.S. Cl. ..................... 378/121; 378/45; 378/136; 378/207
(58) Field of Search .............................. 378/44, 45, 48, 378/49, 119, 121, 136, 138, 207

Primary Examiner—David P. Porta
Assistant Examiner—Therese Barber
(74) Attorney, Agent, or Firm—Jeffrey A Hall

(57) ABSTRACT

A portable x-ray fluorescence spectrometer apparatus comprising a housing; a high voltage energized x-ray source operably secured within the housing; and an unheated electron cathode, operably linked to the high voltage energized x-ray source, thereby eliminating the need for a cathodic electron power supply for spectrometric analysis. Another embodiment comprises a portable x-ray fluorescence spectrometer having a housing, an integrated x-ray tube, a high voltage power supply operably linked to the integrated x-ray tube, and a mechanism for controlling the x-ray emissions of the x-ray tube and power supply including an electron suppression grid operably positioned between a filament cathode and a target anode of the x-ray tube.

4 Claims, 1 Drawing Sheet

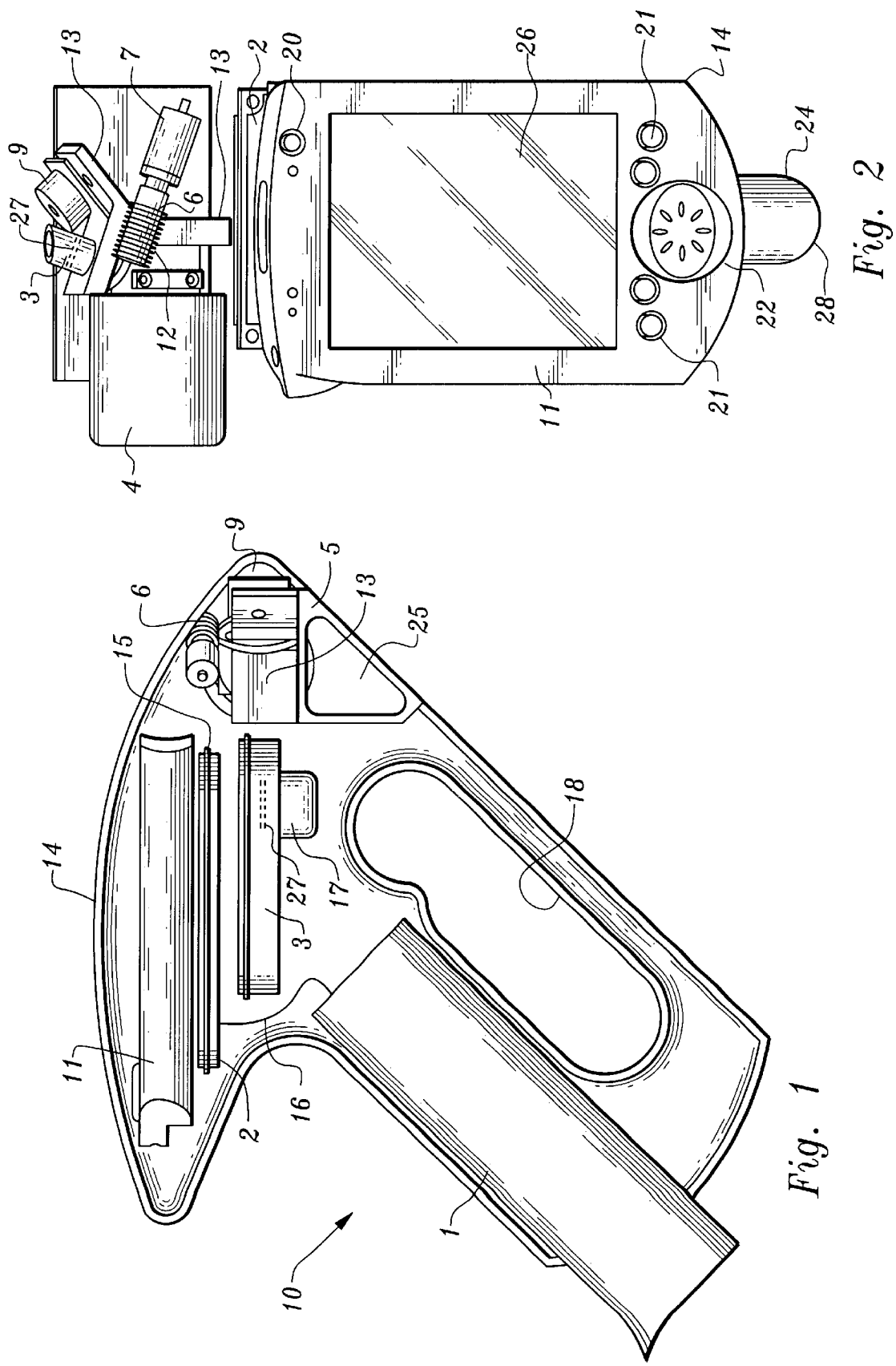

PORTABLE X-RAY FLUORESCENCE SPECTROMETER

CROSS-REFERENCE TO RELATED APPLICATIONS

This application is related to and claims priority from U.S. Provisional Patent application Serial No. 60/255223, filed Dec. 12, 2000.

BACKGROUND OF THE INVENTION

1. Field of Invention

This invention relates to the field of x-ray fluorescence inspection apparatuses and in particular to portable x-ray fluorescence spectrometers.

2. Description of Related Art

Heretofore various x-ray fluorescence spectrometers have been proposed and developed for elemental analysis. In these devices, the sample has been excited by employing either a radioactive isotope or an x-ray tube. Obsolescence of the use of a radioactive isotope is discussed in U.S. Pat. No. 5,528,647 and in which a method for using an x-ray tube in conjunction with a filtering mechanism is described. Due to increasing environmental and governmental requirements and regulations, the use of radioactive isotopes for excitation purposes has not been favored in the design of these devices. With respect to portable x-ray spectrometers, the need for a lightweight, and a low cost unit have forced the designer to continue to employ radioactive isotopes as the excitation source. This has the disadvantage of both increased environmental and safety compliance issues associated with the radioactive source as well as the disadvantage of the lack of control over the excitation characteristics of the source. The inability to control the excitation parameters of the radioactive source is a hindrance for the use of the apparatus for certain applications where excitation selectivity is required. More recent approaches to this limitation have resulted in apparatus that no longer contains a radioactive isotope as the excitation source but employs a thermionic x-ray tube. The x-ray tube is powered by an on-board high voltage supply as well as a filament supply necessary to heat the thermionic cathode. These components are separate components linked by a high voltage cable, typically operating in a manner such that heat dissipation from the isolated anode limits extended use of the device. This also results in a unit which is much larger, heavier and more costly than portable x-ray fluorescence spectrometers which rely on radioactive isotopes for excitation. Predominately, these portable devices are limited for single purpose use, such as transition element identification and quantification for the purposes of alloy identification.

Accordingly, several objects and advantages of the invention are: (1) The use of an x-ray tube coupled with a high voltage power supply in a single lightweight integrated component. This eliminates the need for a radioisotope as the excitation source as well as mitigates the disadvantages of prior systems which employed x-ray tubes and high voltage power supplies as separate components resulting in a device considered too heavy for portable x-ray spectroscopy. (2) The use of a cold cathode x-ray tube for portable x-ray spectroscopy. This allows for the elimination of the thermionic cathode and its associated power supply, thus, reducing the amount of power, weight and heat required as compared to previously portable x-ray spectrometers. (3) The use of an integrated emission extraction and/or suppression grid placed between the non-thermionic cathode and the target anode. This allows for the accurate control of both emission current as well as introduces high emission current stability through the integrated feed back loop between the control grid voltage and the total electron beam emission current. (4) The use of compact, lightweight SMT electronic boards in conjunction with digital signal processing micro controllers. This allows for complex spectral processing on the portable device providing the possibility of addressing multiple applications rather than previous application specific devices. Furthermore, through the use of multiple layer surface mount electronic boards, the overall volume requirement is reduced resulting in a smaller and lighter device than previous devices. (5) The use of an integrated embedded personal computer and associated color LCD display in conjunction with a graphical user interface. This allows for comprehensive on-board software to address multiple tasks, such as qualitative analysis, quantitative analysis, alloy identification, unknown analysis, presented in a familiar Microsoft Windows CE operating system. This integration further mitigates the limitations imposed by smaller; memory limited micro controllers, allowing for a comprehensive x-ray spectroscopy system in a portable device. (6). The use of an ergonomic design which balances the center of gravity in a neutral position on the wrist. This allows the user to see the display during analysis while allowing for extended operation of the device in an ergonomically correct orientation. (7) The use of a docking station coupled with a desktop personal computer in conjunction with a graphical user software system designed to perform extended operations not practical in a portable x-ray spectrometer. This allows for multiple applications to be developed on a single device, such as alloy identification, wood preservative analysis, plastic filler analysis, forensic analysis applications, and other applications suitable for x-ray fluorescence spectroscopy. This object also allows for comprehensive results storage and reporting as well as the control of resident applications on the portable x-ray spectrometer. This objective also allows for the operation of the device is a desktop laboratory fashion. In this manner a sample for analysis may be brought to the spectrometer for analysis rather than the portable spectrometer needing to be position on the sample for analysis. In this manner, the device can be operated as a laboratory grade spectrometer for new method development as well as for those applications where sample stability and precision are at issue. Further objects and advantages of this invention will become apparent from a consideration of the drawings and ensuing description.

Additional objects and advantages of the invention will be set forth in the description which follows, and in part will be obvious from the description, or may be learned by practice of the invention. The objects and advantages of the invention may be realized and obtained by means of the instrumentality's and combinations particularly pointed out in the appended claims.

SUMMARY OF THE INVENTION

To mitigate such limitations a portable x-ray spectrometer is disclosed, which comprises an x-ray tube based upon a non-thermionic cathode in conjunction with the use of energy filtration, supplied as a primary beam filter placed between the x-ray tube output and the sample to be analyzed. The apparatus uses a novel approach to the required high voltage electronics to reduce the size and weight of the overall device by integrating the x-ray tube and high voltage power supply into a single lightweight, low volume, component. Furthermore, as the x-ray tube employs a cold-cathode design, no x-ray filament power supply is required, thereby eliminating weight, heat, and cost. Selective excitation of the sample is determined by a control grid integral to the x-ray tube and controlled by the integrated power supply through a feed back loop. Further refinement of the primary excitation beam is provided through the use of a multi position primary beam filter.

In designing a portable x-ray spectrometer for applications such as alloy identification, size, weight and cost play an important role. To achieve all three of these constraints, novel technology must be employed in concert. This involves eliminating sources of heat and weight while focusing on reduced manufacturing costs. This leads to a design, which integrates multiple surface mount technology (SMT) electronic boards to minimize size and power consumption. As such, the invention employs SMT electronic boards coupled with programmable digital signal processing (DSP) for the complex sorting of energy specific pulses from the x-ray detector. The overall size of the multi channel analyzer (MCA) and analog processing control board is kept to below 2.5 square inches. Further emphasis is placed on the integration of the x-ray tube and the high voltage power supply to minimize weight whilst providing required high voltage standoff of a 35 kV x-ray tube based system. The invention incorporates a grounded target design to maximize heat dissipation from the x-ray tube anode to the case. This results in the need for a high voltage power supply operated in a negative mode with an isolated control grid placed between the non-thermionic cathode and the target anode. The overall size of the high voltage power supply and isolated control grid power supply are kept to a minimum through SMT resulting in a combined supply of 4.75 cubic inches total volume.

As the present invention is intended for use by non-skilled workers, the user interface plays a critical role. As such, the integration of an embedded personal computer coupled with a high-resolution color liquid crystal display is employed. In conjunction the invention integrates this hardware with Microsoft Windows CE operating system platform to provide the user with an integrated graphical user interface for operation of the device. Furthermore, the invention provides for the integration of the portable x-ray spectrometer to a desktop personal computer and associated graphical user interface by the means of a docking station. This docking station consists of a mechanism for operation of the device as a bench top/laboratory based spectrometer, as well as integration with the desktop personal computer. In this manner, the user is able to perform more complex tasks not available on the portable device itself, such as results storage and management, results reporting, application development and method setup. The invention allows for new analytical method development to be performed in conjunction with the desktop personal computer and associated software and for the download of necessary operational information to the portable x-ray spectrometer. In this manner, the user is able to perform multiple analysis of different materials, bound by limitations of the x-ray fluorescence technique and not by limitations imposed by the on board computer memory.

BRIEF DESCRIPTION OF THE DRAWINGS

FIG. 1, is a side view a portable x-ray fluorescence spectrometer, according to the invention of the invention.

FIG. 2, is a top view of such portable x-ray fluorescence spectrometer, according to the invention.

DETAILED DESCRIPTION OF THE INVENTION

In FIG. 1 a preferred embodiment of the portable x-ray fluorescence spectrometer 10, with housing 14, of the present invention is shown. A lithium ion battery pack 1 is preferably the source of power for the invention and is positioned within spectrometer 10 above aperture 18, in one embodiment. The rechargeable battery pack is used to power the entire invention and is operably connected by wires 16, to the power distribution circuit board 2, through which power, preferably 14.8V is distributed to the other components. The high voltage power supply 3, is operably linked to transformer 17, and is preferably rated for 14.8V input and through multipliers raises the voltage to a preferred range of about 4 kV–30kV output. The high voltage power supply 3, also contains an electron control grid 27, which is used to regulate the emission current of the cold cathode x-ray tube 4, best seen in FIG. 2.

The high voltage power supply is preferably designed to operate in negative mode, whereby the electron emission cathode and emission control grid 27, float to high voltage. In this manner the x-ray tube 4, is operated in a grounded anode fashion allowing for heat dissipation through the integrated heat sink 5. An aperture 25, in housing 14, is seen positioned beneath heat sink 5, but may be otherwise positioned or eliminated in other embodiments. Selective excitation of the sample is controlled both by the emission current as well as the primary beam filter 6. The primary beam filter has three user selectable filter locations and is driven to the correct position via a DC servo encoded motor 7, and worm gear drive mechanism 12. The x-rays generated by the cold cathode x-ray tube 4 are preferably collimated through an Al lined collimator 8. The sample is excited by the collimated x-rays and the corresponding fluoresced x-rays characteristic of the elemental composition of the material to be analyzed are collected by the silicon pin (SiPin) in diode detector 9, mounted to holding frame 13. The processed x-rays are amplified by the detector 9, and the corresponding low voltage signals are passed to the amplifier, ADC and multi-channel analyzer and micro controller, located on the post detector processing circuit board 15. Once converted to digital values, the processed signal is sent to the personal data assistant (PDA) embedded micro controller 11, and screen 26. PDA on/off button 20, PDA function buttons 21, PDA cursor control 22, PDA connector 24, and docking station 28, are linked to a control board and are seen in FIG. 2. The processed signal is fed into integrated software for conversion into percent concentration using a fundamental parameter quantitative analysis software algorithm.

As is evident from the above description, a wide variety of spectrometers may be envisioned from the device described herein and additional advantages and modifications will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. An x-ray fluorescence spectrometer apparatus comprising:

a housing;

a high voltage energized sealed x-ray tube, utilizing an unheated electron cathode operated in a grounded anode mode allowing heat dissipation through an integrated heat sink, said energized sealed x-ray tube having an integrated emission control secured within said housing;

a collimator for collimating x-rays generated by said unheated electron cathode positioned in said housing;

an emission/suppression grid positioned between said unheated electron cathode and a target anode, whereby the need for a cathodic electron power supply for spectrometric analysis is eliminated;

a diode detector secured within said housing; and an amplifier being linked to a multi-channel analyzer and a microcontroller, for converting low voltage signals from said diode detector into digital signals which are transmitted to a personal data assistant embedded in said micro controller.

2. The x-ray fluorescence spectrometer of claim 1, further including surface mount SMT electronic boards specific for x-ray detection and including means for digital signal processing located on a post detector processing circuit board and positioned in said housing in close proximity to said high voltage energized sealed x-ray tube.

3. A portable x-ray fluorescence spectrometer, comprising:

a housing;

an integrated x-ray tube secured within said housing;

a high voltage power supply linked to said integrated x-ray tube;

means for controlling the x-ray emissions of said integrated x-ray tube and a power supply including an electron suppression grid positioned between non-thermonic cathode and a target anode of said integrated x-ray tube, thereby eliminating the need for utilizing radioactive isotopes for x-ray fluorescence spectrometric analysis;

a primary beam filter for selective excitation of an electron generating sample being secured within said housing;

a collimator for collimating x-rays generated by said unheated electron cathode being positioned in said housing;

a diode detector secured within said housing; and an amplifier being linked to a multi-channel analyzer and a microcontroller, for converting low voltage signals from said diode detector into digital signals which are transmitted to a personal data assistant embedded in said micro controller.

4. The portable x-ray fluorescence spectrometer of claim 3, further including surface mount SMT electronic boards specific for x-ray detection and including means for digital signal processing located on a post detector processing circuit board and positioned in said housing in close proximity to said integrated x-ray tube.

* * * * *